(12) United States Patent
Fehér et al.

(10) Patent No.: US 7,396,128 B2
(45) Date of Patent: Jul. 8, 2008

(54) PROCESS AND APPARATUS FOR EXAMINING THE VISUAL FUNCTIONS OF THE EYE

(76) Inventors: János Fehér, Tárogató lejto 8, Budapest H-1021 (HU); Ákos Fehér, Tárogató lejto 8, Budapest H-1021 (HU)

( * ) Notice: Subject to any disclaimer, the term of this patent is extended or adjusted under 35 U.S.C. 154(b) by 0 days.

(21) Appl. No.: 10/561,434

(22) PCT Filed: Jun. 18, 2004

(86) PCT No.: PCT/HU2004/000060

§ 371 (c)(1),
(2), (4) Date: Dec. 8, 2006

(87) PCT Pub. No.: WO2004/112597

PCT Pub. Date: Dec. 29, 2004

(65) Prior Publication Data

US 2007/0182929 A1 Aug. 9, 2007

(30) Foreign Application Priority Data

Jun. 20, 2003 (HU) .................................. 0301899

(51) Int. Cl.
*A61B 3/10* (2006.01)
*A61B 3/00* (2006.01)
(52) U.S. Cl. .................. 351/205; 351/200; 351/246

(58) Field of Classification Search ......... 351/200–205, 351/221, 222, 237, 246
See application file for complete search history.

(56) References Cited

U.S. PATENT DOCUMENTS

| 3,992,087 | A | * | 11/1976 | Flom et al. | 351/210 |
|---|---|---|---|---|---|
| 4,545,658 | A | * | 10/1985 | Weiss | 351/222 |
| 4,838,684 | A | | 6/1989 | Smith | 351/239 |
| 5,550,602 | A | * | 8/1996 | Braeuning | 351/243 |
| 5,953,102 | A | | 9/1999 | Berry | 351/247 |
| 6,176,581 | B1 | | 1/2001 | Newsome | 351/224 |
| 6,293,675 | B1 | | 9/2001 | Eger | 351/224 |

FOREIGN PATENT DOCUMENTS

DE 736 340 C 6/1943

* cited by examiner

*Primary Examiner*—Mohammed Hasan
(74) *Attorney, Agent, or Firm*—Birch, Stewart, Kolasch & Birch, LLP

(57) ABSTRACT

The visual function is determined with the help of test images, comprising inducing photostress induced by illuminating the eye with an intense light, then measuring the time needed for the recovery of the visual function before the illumination. The test images are periodically moving test images, and the visual function is determined on the basis of detecting the phenomenon of optokinetic nystagmus. According to another process the visual function is determined by measuring critical fusion frequency (CFF) before and after the photostress.

7 Claims, 2 Drawing Sheets

PROCESS AND APPARATUS FOR EXAMINING THE VISUAL FUNCTIONS OF THE EYE

FIELD OF THE INVENTION

The subject of the invention is a process and apparatus for examining the visual functions of the eye. Specifically the invention relates to a new ophthalmologic diagnostic process and instrument, which makes it possible to determine visual functions objectively and measure the recovery time of visual functions following intensive illumination. By using the invention the early signs of sight damage can be recognised.

BACKGROUND OF THE INVENTION

The fact that after intensive illumination (so-called photostress) a certain period of time is needed for the visual functions of the eye to return to the level before the illumination is well known from the art. The biological explanation to the phenomenon is that light induces a change in the chemical structure of the visual purple (the photoperceptive material of the eyes) and it temporarily loses its photoperceptive ability. Under normal circumstances the original light sensitivity of the visual purple returns in a fraction of a second. However, as a result of intensive illumination and in the case of certain diseases this recovery time is significantly longer (Magdar J. Am. J. Ophthalmology, 1962, 49:147-150; Forsius H., Eriksson AW, Krause U. Acta Ophthalmologica, 1963, 41: 55-63; Glaser JS, Savino PJ, Sumers KD, McDonald SA, Krighton RW Am. J. Ophthalmology, 1977, 83: 255-260). Diseases resulting in the disturbance of the regeneration of the visual purple and the lengthening of the recovery time of the visual functions are rather common. Such diseases include first of all the senile degeneration of the central part of the retina, retinopathy associated with serious short-sightedness, diabetes and vascular sclerosis. A large number of other eye diseases and the lasting use of certain drugs may also cause visual complaints. Presently not much attention is paid to solving this problem, first of all because no appropriate apparatus is available.

Optokinetic nystagmus is a physiological phenomenon known for decades (Catford, G.V., Oliver, A. Proo $2^{nd}$ International Orthoptic Congress, Excerpta Medica Amsterdam, 1971). Essentially it means that the eyes involuntarily, automatically follow the movement of objects or images perceived in their visual field. If the movement is periodic, the eyeballs also move there and back with the same frequency as the perceived object (and this pendular oscillation of the eye is called nystagmus). Or the other way round, if the eye moves, it sees the moving object, but if it stays still, then it does not.

Another known phenomenon is that they eye can perceive the flashes of a vibrating light source separately only to a certain frequency. If the frequency of the flashes is higher than this, the eye perceives the vibrating light signals merged, as constant light. This frequency is called critical fusion frequency (CFF).

In the laser surgery of the cornea an instrument called "eye-tracker" is used to follow the position of the eye during the operation. This instrument perceives the position of the eye and controls a laser knife. The laser knife works as long as the eye is motionless, and it stops as soon as the eye moves away from its position called mid-position.

The adaptometer is a known ophthalmologic diagnostic instrument used for measuring the dark adaptation of the eye. When using it, after staying in complete darkness for ten minutes three minutes of continuous illumination is used with white light. The amount of illumination is 2,000-3,000 lux. After this an image of certain brightness just not visible to the examined person occurs periodically in front of the eye. When after a certain period of time the person perceives the picture, another image occurs, which is illuminated less by one logarithmic grade. After some more time the examined person will also recognise this image; then a new image appears, which is illuminated at an even weaker extent. It goes on like this for 45 minutes. The extent of adaptation is the sign or image illuminated at the weakest extent, which the, eye can still recognise in the course of the 45-minute examination (Goldman, M.H.: Un nouvel adaptometre automatique. Bull Soc. Franc Optalmol 1950, 63:4-17). This apparatus is not sensitive enough, it is suitable to indicate only rough differences, Besides the examination is very lengthy, especially if the two eyes are examined separately. It is not a common examination of the everyday practice.

The nyctometer is a known device used for determining the light adaptation of the eye (Hartman E, Wehmeyer K.: Klinische Monatsblatter für Augenheilkunde, 1980, 176:859-863). In this case test images of the same size are used, but they are illuminated in a different way as compared to the background. Eight different variations can be used, where the proportions of the illumination of the background and the image are the following: 1:23, 5; 1:4, 87; 1:2, 71; 1:2, 00; 1:1, 66; 1:1, 46; 1:1, 25; 1:1, 14. The aim of the examination is to determine the image illuminated at the least extent, which the examined person can still recognise. This apparatus has another version with a built-in clock; and it is also suitable for measuring the time needed to recognise the image illuminated at the least extent. This apparataus is not suitable for the objective determination of visual functions, and it has a rather restricted indication field, and for these reasons it is not widely used in practice.

The object of the invention was to create a new process and apparatus, which, by means of examining the visual functions of the eye under standardised.: circumstances, make it possible to recognise the early signs of visual damage of ophthalmologic and non-ophthalmologic origin.

SUMMARY OF THE INVENTION

The set task is solved with a process according to the invention, in the course of which with the help of test images the visual function is determined, photostress is induced by illuminating the eye with an intense light, then the time needed for the recovery of the visual function before the illumination is measured. According to the process periodically moving test images are used, and the visual function is determined on the basis of detecting the phenomenon of optokinetic nystagmus.

The invention also relates to an alternative process in the course of which the visual function is determined by measuring critical fusion frequency (CFF) before and after the photostress.

The invention extends to an apparatus which contains a light source suitable for illuminating a test image and inducing photostress, a test image that can be illuminated with the light source, an optical device projecting the light of the light source and/or the picture of the test image into the eye and a clock measuring the time of the examination, and it has a test unit suitable for moving and changing test images and a measuring unit electrically connected to the test unit, which contains a nystagometer sensing the movement of the eye and a display unit and time measuring unit connected to it.

Preferably the test unit is constructed as a rotatable mechanic device, or it is equipped with a monitor displaying test images. Expediently there is a replaceable filter between the light source and the test unit.

Another version of the apparatus contains a light source suitable for inducing photostress and a test unit constructed as a light source vibrating with variable frequency.

The invention is described in detail on the basis of an example and a drawing.

DETAILED DESCRIPTION OF THE INVENTION

In the course of a process according to the invention the visual function is determined with the help of test images. The test images can be for example figures used for examining visual acuity (optotype), which are letters, numbers, pictures or figures decreasing according to a certain scale (e.g.: decimal or angular minute); images used for examining contrast sensitivity, which are letters, numbers, pictures or figures of the same size but a decreasing contrast; images used for examining colour vision, which are letters, numbers, pictures or figures made up of small, colour round shapes; and boards containing a combination of the above (e.g.: the size and contrast of the images change at the same time, or the size and contrast of the colour image changes too, etc.).

As opposed to the present practice, which uses static test images to measure visual function, in our case moving (dynamic) test images are used. It makes the objective determination of vision possible on the basis of evaluating the phenomenon of optokinetic nystagmus described in the introduction part, which has not been used in any apparatus so far.

Figure 1:
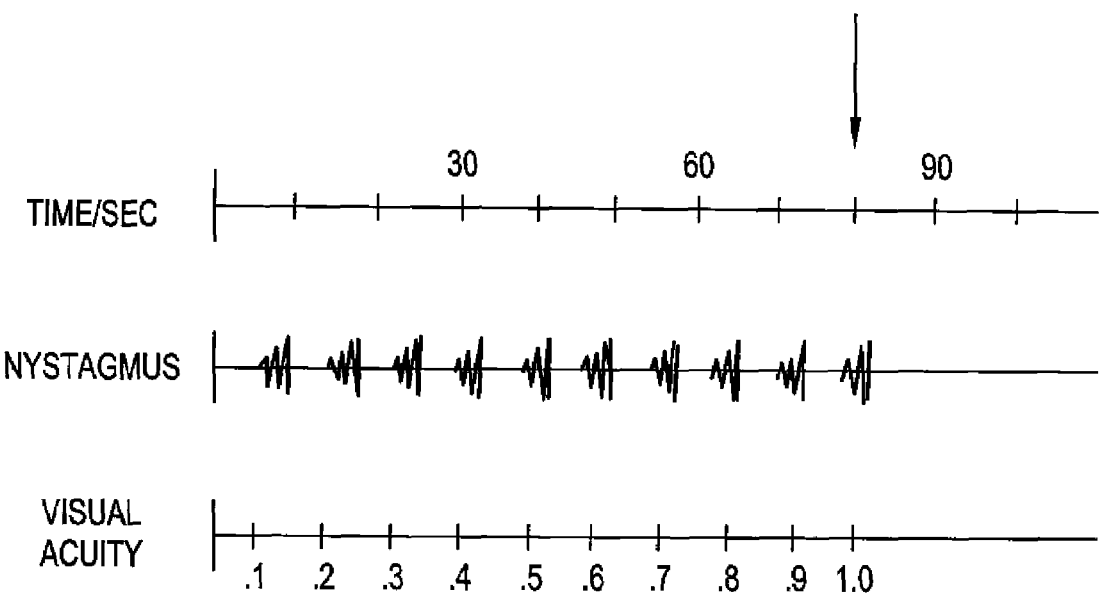
FIG. 1: is a diagram showing visual acuity determination performed on the basis of the phenomenon of optokinetic nystagmus.

The diagram in FIG. 1 illustrates the determination of visual acuity on the basis of the phenomenon of optokinetic nystagmus. In the top line of the diagram the period of the examination is shown. The central line shows nystagmus: the examined person is shown periodically moving test images, which he/she finds more and more difficult to recognise, and on the basis of evaluating his/her nystagmus it is determined whether he/she can see the image. In the case shown here the nystagmus of the examined person can be detected up until the test image that corresponds to visual acuity 1.0, that is the examined person can still see this image, so his/her visual acuity is 1.0. The values of visual acuity (visus) are shown in the bottom line of the diagram.

After determining visual acuity the eyes are illuminated with an intense light and photostress is induced, then visual acuity is measured as described above. It can be seen in FIG. 2 that the visual function before the photostress returns only slowly, more and more time is needed for recognising images of an increasingly finer resolution. In the present example more than eighty seconds after the photostress visual acuity only reaches a value of 0.6.

Preferably the two eyes should be examined separately. If there is a refractional problem, the sight test is carried out with appropriate glasses or contact lenses.

In the case of a variation of the process according to the invention before and after the photostress the visual function is determined by measuring critical fusion frequency (CFF). The frequency of vibration can be changed optionally between 1 and 50 Hz. The critical value is the frequency perceived by the eye as continuous light.

Figure 3:
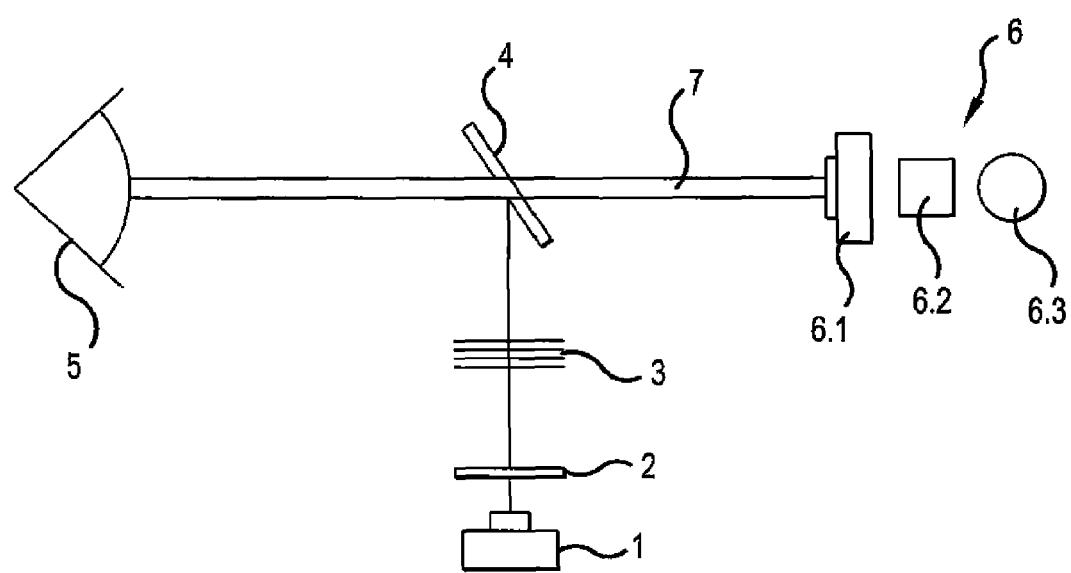
FIG. 3: is the diagram of a preferred construction of the apparatus according to the invention.

FIG. 3 shows the diagram of a favourable construction of the apparataus according to the invention. Through a replaceable filter 2 a light emitted by a light source 1 also suitable for inducing photostress illuminates a test image placed in the test unit 3 suitable for moving and changing test images, and the picture of the image is projected into the examined eye 5 by a mirror 4 or some other suitable optical device. Opposite the eye 5 there is a measuring unit 6, which contains a nystagmometer 61 detecting the nystagmic movement of the eye 5, a display unit 62 and a clock 63, which measures the time of the examination and is electrically connected to the test unit 3. The nystagmometer 61—which is a device similar to an "eye tracker" used in laser surgery for following the position of the eye, as mentioned in the introduction part—emits a radar ray 7 through a mirror 4 into the examined eye 5 in a state of rest, and receives the reflected signal with a sensor. The radar ray 7 can be visible light, infrared ray, radar or other radio wave. The display unit 62 connected to the nystagmometer 61 and equipped with a clock 63 shows when the eye 5 moves. On the basis of the reflected signal the nystagmometer also controls the test unit 3 the examined person detects the given test image, that is the eye moves from its mid-position, the nystagmometer 61 gives an automatic instruction to display the next test image, which is always more difficult to recognise.

Figure 2:
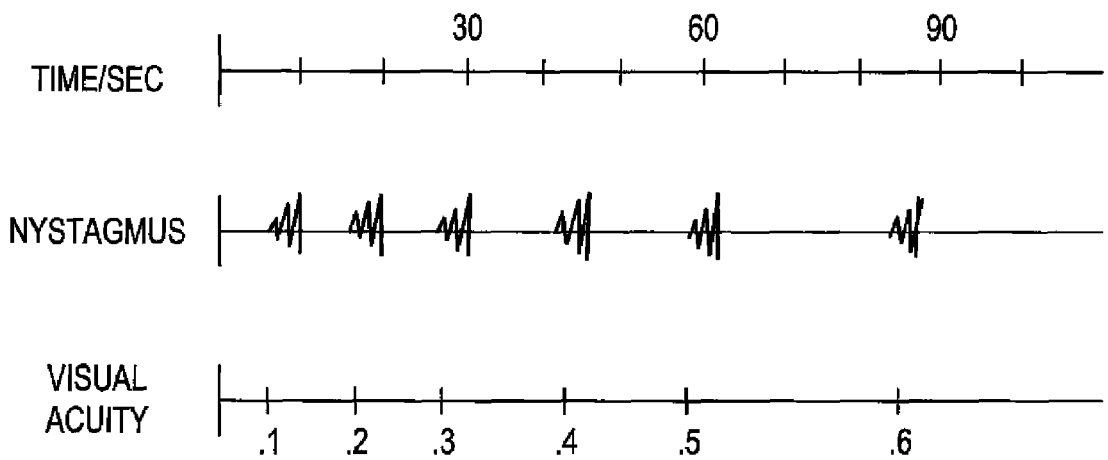
FIG. 2: is a diagram in accordance with FIG. 1, after photostress.

The display unit 62 shows three data at the same time: the data of the test image (e.g.: visual acuity), it receives the impulses coming from the nystagmometer 61 (that is whether there is or there is not nystagmus) and finally it measures the time of the examination with a time measuring unit 63 (seconds, minutes). In principle this display unit 62 is similar to the display unit of a multichannel electrocardiograph or electroencephalograph, and the data is displayed on screen and/or paper-tape, e.g.: as shown in FIGS. 1 and 2.

The light emitted by the light source 1 can be homogenous or focused, depending on whether the whole of the retina or only its central part is intended to be stimulated. The colour of the light can also be changed as required, it can be white, red, green or blue. In the case of white light all photoperceptive cells of the eye 5 can be stimulated, while in the case of using colour light only the cells sensitive to the given light can be stimulated. In the case of a transparent test image the intensity of illumination is 1-10 lux; in order to induce photostress the intensity of illumination is between 500-3,000 lux, favourably between 1,000-2,500 lux, especially favourably between 1,500-2,000 lux. Continuous light is needed to illuminate the test image, while the period of photostress is 10-300 s, favourably 30-180 s, especially favourably 30-60 s.

The parameters of the light source 1 are set at the beginning of the examination by the doctor or the examining person on the basis of a previously determined computer program depending on the demands of the examination. The light source 1 is placed at a 20 cm distance from the eye 5 to avoid heat effect endangering the eye. With the help of a filter 2 placed between the test unit 3 and the light source 1 the colour of the light can be changed both in the case of photostress and sight test.

Practically the test unit 3 is constructed in a way that one of the test images periodically goes past behind a "window" shaped like a lying rectangle (or on a screen), in a horizontal direction. In the course of the examination images are used that are always more difficult to recognise (e.g.: always smaller images). The test image can be moved with a mechanic tool, e.g.: a cylinder rotating behind the "window", and the test image is printed on the shell of this cylinder. In the case of a digitised version the test unit 3 is equipped with a screen displaying the test images, and the test images move on the screen in a horizontal (or vertical) direction.

The test images are situated in front of the eye at a 30 cm distance (reading distance), and they are illuminated with a constant, reflex-free, diffuse light from the front, or in the case of transparent images from the back.

The speed of the test image is selected by the doctor from a previously prepared program, which takes into consideration the characteristics of the patient and the disease.

In addition to the construction of the apparatus described above suitable for carrying out detailed examinations the equipment according to the invention also has further possible versions. For example for simple screenings the apparatus should be practically constructed in a portable form. In this case the measuring unit 6 can be omitted, because if the test image is still, the examined person can read the sign on the picture, and the doctor can manually determine the time (with a stopwatch) needed for the vision to return to the level before photostress was induced (e.g.: the examined person reads the smallest signal he/she read before the photostress). In the case of a further favourable construction the test image in the test unit 3 is replaced by a vibrating light source suitable for measuring critical fusion frequency (CFF) mentioned in the introductory part of this specification.

The most important advantage of the process and apparatus according to the invention is that it is very sensitive, and it can detect eye damage at an early stage of the disease, which with the presently used diagnostic instruments is only possible at a developed stage of the disease. Consequently the invention makes it possible to recognise ophthalmologic and non-ophthalmologic diseases at a very early stage, when treatment can still be successful. The practical use of the invention is increased by the fact that due to the latest research these diseases can be treated, but only in the case that they are diagnosed early enough.

Beside the ophthalmologic and general medical applications the invention can be excellently used in the field of labour hygiene for ability testing in certain professions and for the early detection of potential working place damage. This application can be useful especially in two cases: in the case of those who are permanently exposed to light effect, such as people working with video display terminal and in the case of people permanently working in intensive sunlight. At the same time screening is justified in jobs where toxic materials occur.

The invention claimed is:

1. A process for examining the visual functions of the eye, which comprises:
    determining with the help of periodically moving test images the visual function of the eye, then
    inducing photostress by illuminating the eye with an intense light,
    measuring the time needed for the recovery of the visual function before the illumination, and
    determining the visual function of the eye on the basis of detecting the phenomenon of optokinetic nystagmus.

2. A process for examining the visual function of the eye which comprises;
    determining the visual function of the eye by measuring critical fusion frequency (CFF), then
    inducing photostress by illuminating the eye with an intense light and measuring the time needed for the recovery of the visual function before the illumination by measuring critical fusion frequency (CFF).

3. An apparatus for examining the visual features of the eye which comprises;
    a light source suitable for illuminating a test image and inducing photostress,
    a test image that can be illuminated with the light source,
    an optical device projecting the light of the light source and/or the picture of the test image into the eye,
    a clock measuring the time of the examination,
    a test unit suitable for moving and changing test images, and
    a measuring unit electrically connected to the test unit, which measuring unit contains a nystagometer sensing the movement of the eye and a display unit and time measuring unit connected to the test unit.

4. The apparatus as claimed in claim 3, wherein the test unit is constructed as a rotatable mechanic device.

5. The apparatus as claimed in claim 3, wherein the test unit is equipped with a screen displaying test images.

6. The apparatus as claimed in claim 3, wherein there is a replaceable filter between the light source and the test unit.

7. The apparatus as claimed in claim 3, wherein the test unit is constructed as a light source vibrating with variable frequency.

* * * * *